US012514973B2

(12) United States Patent
Helmer et al.

(10) Patent No.: US 12,514,973 B2
(45) Date of Patent: Jan. 6, 2026

(54) DRUG DELIVERY DEVICE WITH A CAP

(71) Applicant: Sanofi-Aventis Deutschland GMBH, Frankfurt am Main (DE)

(72) Inventors: Michael Helmer, Frankfurt am Main (DE); Winfried Huthmacher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 354 days.

(21) Appl. No.: 18/083,897

(22) Filed: Dec. 19, 2022

(65) Prior Publication Data

US 2023/0124341 A1 Apr. 20, 2023

Related U.S. Application Data

(63) Continuation of application No. 15/778,503, filed as application No. PCT/EP2016/078276 on Nov. 21, 2016, now Pat. No. 11,571,505.

(30) Foreign Application Priority Data

Nov. 27, 2015 (EP) .................................... 15196713

(51) Int. Cl.

*A61M 5/00* (2006.01)
*A61M 5/24* (2006.01)
*A61M 5/32* (2006.01)

(52) U.S. Cl.

CPC .......... *A61M 5/001* (2013.01); *A61M 5/2466* (2013.01); *A61M 5/3204* (2013.01);
(Continued)

(58) Field of Classification Search

CPC .... A61M 5/001; A61M 5/2466; A61M 5/288; A61M 2005/2474; A61M 5/3204;
(Continued)

(56) References Cited

U.S. PATENT DOCUMENTS 2,020,828 A 11/1935 Goldberg
2,461,481 A 2/1949 Roehr
(Continued)

FOREIGN PATENT DOCUMENTS

CN 2224628 4/1996
CN 101801435 8/2010
(Continued)

OTHER PUBLICATIONS

International Preliminary Report on Patentability in International Appln. No. PCT/EP2016/078276, dated May 29, 2018, 6 pages.
(Continued)

*Primary Examiner* — Nilay J Shah
(74) *Attorney, Agent, or Firm* — Bond, Schoeneck & King, PLLC

(57) ABSTRACT

A needle assembly for use with a drug delivery device comprises a cap releasably secured to the drug delivery device and a blocking member. The blocking member comprises a disinfectant swab and a user graspable portion. The blocking member is configured to be physically moved with respect to the needle assembly by a user. The needle assembly is configured such that in an initial position, the blocking member blocks the cap from being removed from the drug delivery device and movement of the blocking member from the initial position causes the disinfectant swab to contact a septum of a cartridge retained within the drug delivery device.

22 Claims, 7 Drawing Sheets

(52) U.S. Cl.
CPC ..... *A61M 5/326* (2013.01); *A61M 2005/2474* (2013.01); *A61M 5/3245* (2013.01); *A61M 5/3257* (2013.01)

(58) Field of Classification Search
CPC .............. A61M 5/3213; A61M 5/3243; A61M 5/3245; A61M 5/3257; A61M 2005/3258
See application file for complete search history.

(56) References Cited

U.S. PATENT DOCUMENTS

| | | | | |
|---|---|---|---|---|
| 3,739,779 | A * | 6/1973 | Pfleger | A61M 5/288 604/274 |
| 3,977,401 | A | 8/1976 | Pike | |
| 4,031,889 | A | 6/1977 | Pike | |
| 5,069,669 | A | 12/1991 | Kole | |
| 5,342,319 | A * | 8/1994 | Watson | A61J 1/2096 604/167.02 |
| 6,994,315 | B2 * | 2/2006 | Ryan | A61M 39/26 251/149.6 |
| 2004/0014781 | A1 | 1/2004 | Elger et al. | |
| 2005/0027259 | A1 | 2/2005 | Vetter et al. | |
| 2012/0041384 | A1 | 2/2012 | Finke et al. | |
| 2013/0085474 | A1 * | 4/2013 | Charles | A61M 39/162 604/218 |
| 2013/0226143 | A1 | 8/2013 | Davies et al. | |
| 2015/0005734 | A1 | 1/2015 | Inoue et al. | |
| 2015/0231289 | A1 | 8/2015 | Webb | |
| 2020/0297917 | A1 | 9/2020 | Helmer et al. | |

FOREIGN PATENT DOCUMENTS

| | | |
|---|---|---|
| CN | 101945681 | 1/2011 |
| CN | 102119037 | 7/2011 |
| CN | 102125711 | 7/2011 |
| CN | 102834134 | 12/2012 |
| CN | 103619381 | 3/2014 |
| CN | 104010615 | 8/2014 |
| CN | 104023768 | 9/2014 |
| CN | 104812426 | 7/2015 |
| CN | 104884106 | 9/2015 |
| EP | 2554207 | 2/2013 |
| GB | 770341 | 3/1957 |
| JP | 2000-354627 | 12/2000 |
| JP | 2004-305720 | 11/2004 |
| JP | 2012-500679 | 1/2012 |
| JP | 2013-533096 | 8/2013 |
| JP | 2013-542021 | 11/2013 |
| JP | 2013-542792 | 11/2013 |
| JP | 2014-532517 | 12/2014 |
| JP | 2015-533603 | 11/2015 |
| WO | WO 2001/091797 | 12/2001 |
| WO | WO 2009/002474 | 12/2008 |
| WO | WO 2009/091707 | 7/2009 |
| WO | WO 2009/150078 | 12/2009 |
| WO | WO 2010/022870 | 3/2010 |
| WO | WO 2012/021762 | 2/2012 |
| WO | WO 2012/059449 | 5/2012 |
| WO | WO 2012/059455 | 5/2012 |
| WO | WO 2012/158135 | 11/2012 |
| WO | WO 2013/066742 | 5/2013 |
| WO | WO 2014/076225 | 5/2014 |
| WO | WO 2014/080020 | 5/2014 |
| WO | WO 2014/096957 | 6/2014 |

OTHER PUBLICATIONS

International Search Report and Written Opinion in International Appln. No. PCT/EP2016/078276, mailed Jan. 30, 2017, 9 pages.

* cited by examiner

DRUG DELIVERY DEVICE WITH A CAP

CROSS REFERENCE TO RELATED APPLICATIONS

This application is a continuation application of U.S. application Ser. No. 15/778,503, filed on May 23, 2018, which is a U.S. national stage application under 35 USC § 371 of International Application No. PCT/EP2016/078276, filed on Nov. 21, 2016, which claims priority to European Application No. 15196713.0, filed on Nov. 27, 2015, the entire contents of which are incorporated herein by reference.

TECHNICAL FIELD

The disclosure relates to a drug delivery device having a cap.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Other types of disease require injections using auto-injectors. These injections may be weekly or every two or four weeks. Due to the physical impairment of some users, it is desirable to keep the user interaction required to prepare and operate the injection pen simple and minimal.

SUMMARY

An aspect of the specification provides a needle assembly for use with a drug delivery device, the needle assembly comprising a cap releasably secured to the drug delivery device; and a blocking member comprising a disinfectant swab and a user graspable portion and configured to be physically moved with respect to the needle assembly by a user, wherein the needle assembly is configured such that: in an initial position the blocking member blocks the cap from being removed from the drug delivery device; and movement of the blocking member from the initial position causes the disinfectant swab to contact a septum of a cartridge retained within the drug delivery device.

The blocking member may comprise a removable sterile seal covering the disinfectant swab. Here, the sterile seal may be configured to be physically removed by a user prior to movement of the blocking member, or the sterile seal may be configured to be physically removed by action of removal of the blocking member. The sterile seal may be secured at one end to an outer body of the cap so as to cause removal of the sterile seal from the disinfectant swab, when the blocking member is removed.

The cap may comprise opposing apertures, which the blocking member is configured to pass through and occupy when in the initial position.

The needle assembly may comprise a needle holder and a sleeve, wherein the needle holder is configured to move axially within the sleeve and wherein the sleeve is retained within the cap. The sleeve may comprise one or more resiliently deformable clips configured to retain the needle holder in a first position, and optionally wherein the cap prevents the clips from deforming while the cap is in a secured position.

The needle assembly may comprise a pre-stressed resilient member configured to bias the sleeve and the needle holder apart. The pre-stressed resilient member may be configured to force the needle holder to move axially within the sleeve after the cap has been moved from the secured position to an intermediate position, such that the needle assembly contacts the cartridge retained within the drug delivery device. The engaging features of the cap may comprise a threaded connection to the drug delivery device and wherein at least three full rotations are required to move the cap from the secured position to the intermediate position.

Optionally, when the cap reaches the intermediate position it can be removed from the needle assembly and drug delivery device.

A proximal end of the needle may be surrounded by a compressible spacer material and a cover foil, the cover foil disposed around the compressible spacer and the needle assembly may be configured such that when the needle assembly contacts the cartridge retained within the drug delivery device the compressible spacer material is compressed and the cover foil and cartridge are pierced by the proximal needle end.

A further aspect of the specification provides a medical apparatus comprising: a drug delivery device housing a medicament cartridge, optionally including a medicament; and a needle assembly as above.

A further aspect of the specification provides a method relating to a drug delivery device, the method comprising: a user moving a blocking member from an initial position in which the blocking member blocks a cap from being removed from the drug delivery device to a position in which the blocking member does not block the cap, the movement causing a disinfectant swab forming part of the blocking member to contact a septum of a cartridge retained within the drug delivery device.

The terms “drug” or “medicament” which are used interchangeably herein, mean a pharmaceutical formulation that includes at least one pharmaceutically active compound.

The term “drug delivery device” shall be understood to encompass any type of device, system or apparatus designed to immediately dispense a drug to a human or non-human body (veterinary applications are clearly contemplated by the present disclosure). By “immediately dispense” is meant an absence of any necessary intermediate manipulation of the drug by a user between discharge of the drug from the drug delivery device and administration to the human or non-human body. Without limitation, exemplary injection devices may include, e.g., syringes, autoinjectors, injection pen devices and spinal injection systems.

These and other aspects will be apparent from and elucidated with reference to the embodiments described hereinafter.

BRIEF DESCRIPTION OF THE DRAWINGS

Exemplary embodiments of the present invention are described with reference to the accompanying drawings, in which.

DETAILED DESCRIPTION

Figure 1A:
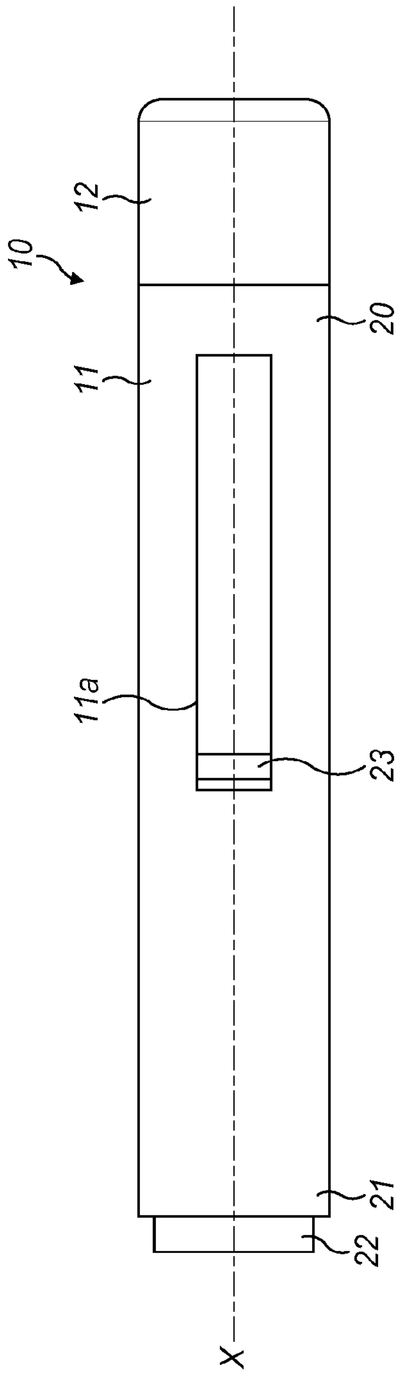
FIG. 1A is a schematic side view of an injection device according to an exemplary embodiment, with a cap attached to a body of the injection device.

One or more embodiments provide a drug delivery device with a needle assembly. A cap is releasably secured to the drug delivery device. A blocking member in an initial position prevents the cap being removed. Removal of the blocking member causes disinfecting of a septum of a medicament cartridge during removal, and after removal the cap can be removed. This causes the septum to be disinfected before use, and can prevent drug delivery using a non-disinfected septum.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
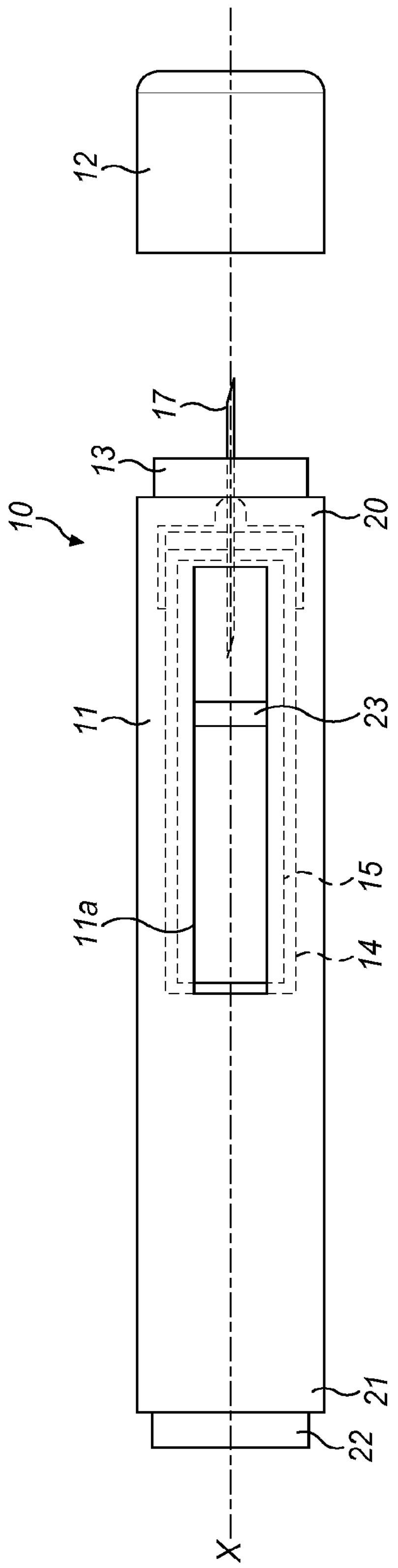
FIG. 1B is a schematic side view of the injection device of FIG. 1A, with the cap removed from the body.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of sleeve 13 relative to housing 11. For example, sleeve 13 can move in a longitudinal direction parallel to longitudinal axis X. Specifically, movement of sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of sleeve 13 by placing a distal end of sleeve 13 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 13.

Another form of insertion is "automated," whereby needle 17 moves relative to housing 11. Such insertion can be triggered by movement of sleeve 13 or by another form of activation, such as, for example, a button 22. As shown in FIGS. 1A & 1B, button 22 is located at a proximal end of housing 11. However, in other embodiments, button 22 could be located on a side of housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament within the syringe, forcing it out of needle 17.

Following injection, needle 17 can be retracted within sleeve 13 or housing 11. Retraction can occur when sleeve 13 moves distally as a user removes device 10 from a patient's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

Figure 2:
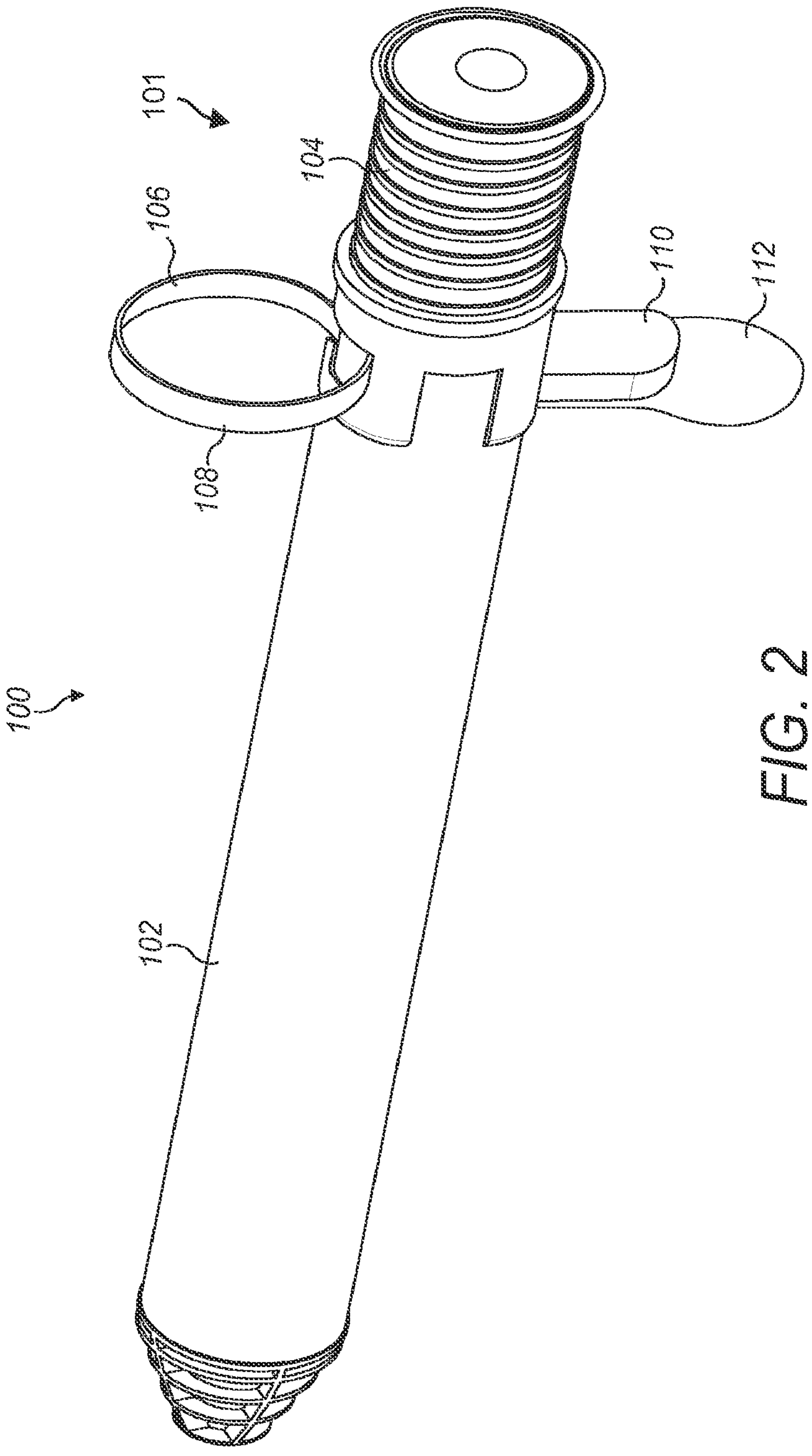
FIG. 2 shows a drug delivery device with a needle assembly attached.

Referring to FIG. 2, a drug delivery device 100 (which is an example of the injector device 10 of FIGS. 1A and 1B) is shown. The drug delivery device 100 comprises a main body 102 (which is an example of the housing 11 of FIGS. 1A and 1B) and a needle assembly 101 (including the needle 17 of FIGS. 1A and 1B).

The needle assembly 101 comprises a cap 104 (which is an example of the cap 12 of FIGS. 1A and 1B) and a removable member 106. The removable member 106 is removable in that is can be separated from the needle assembly 101 and the main body 102 but it may remain coupled to the main body or the cap 104, e.g. by a tether. The removable member is a blocking member, as will be apparent from the below explanation.

The removable member 106 has a user graspable portion 108, which may take the form of a ring. A user may insert a finger or thumb into the ring in order to exert a force on the removable member 106. The removable member also comprises a disinfectant swab 110 and a sterile seal 112, which covers the disinfectant swab 110. The disinfectant swab 110 may be a sponge like material soaked in a medicinal alcohol.

The cap 104 is releasably secured to a distal end of the main body 102 of the drug delivery device 100. Both the main body 102 and cap 104 have a generally cylindrical configuration. The cap 104 has two opposing apertures near its proximal end. The removable member 106 is configured to pass through and occupy these apertures when the cap 104 is secured to the main body 102 such that the user graspable portion 108 and disinfectant swab 110 protrude from opposing sides of the cap 104. The sterile seal 112 may be a foil which is releasably secured to the edges of the disinfectant swab 110 and which has an unsecured portion, which can be grasped by a user to allow the user to remove the sterile seal 112. Alternatively, the sterile seal 112 may have no user graspable protrusion, as explained in greater detail with reference to FIGS. 4 and 5.

Figure 3:
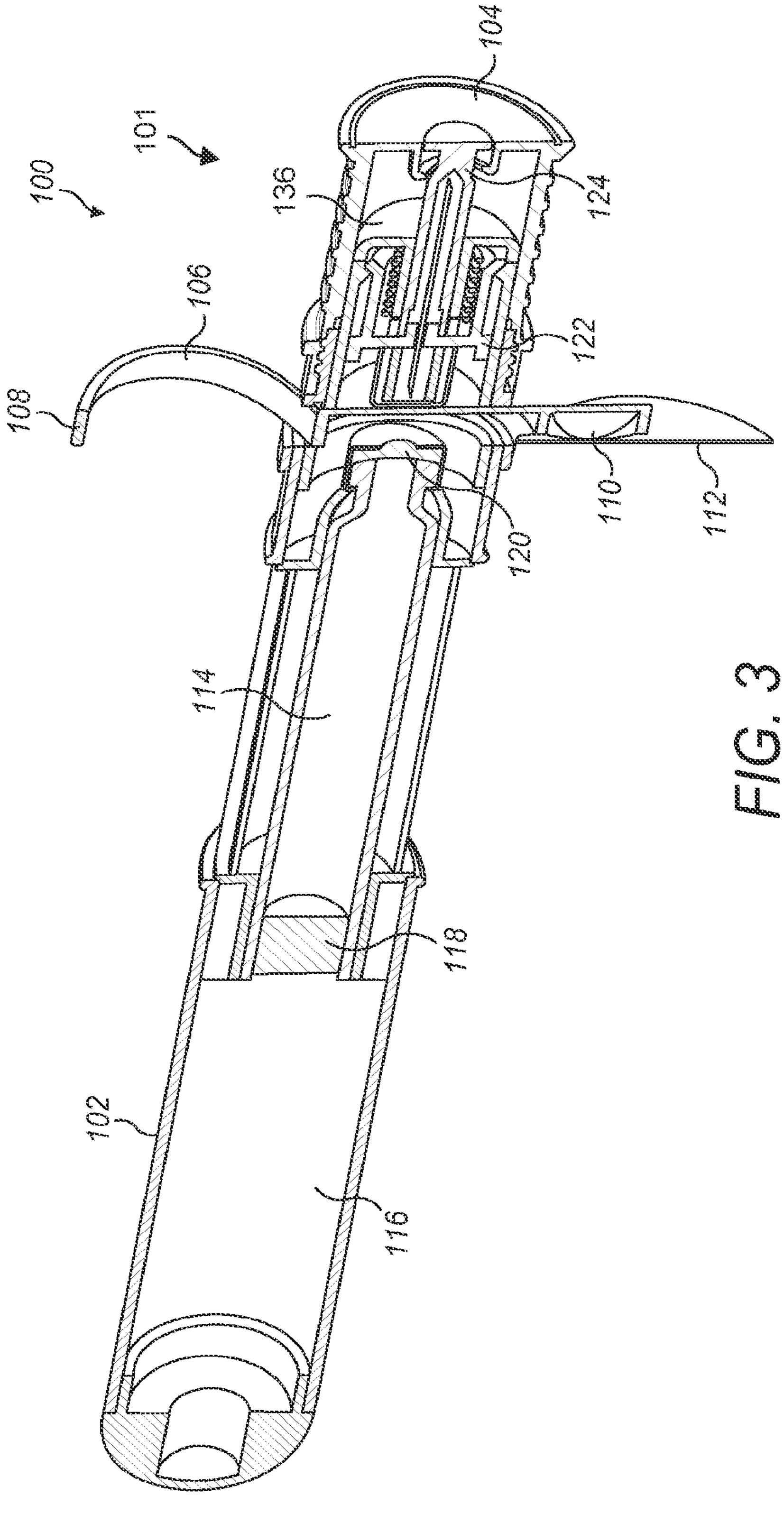
FIG. 3 is a cut away view of the drug delivery device and needle assembly of FIG. 1.

FIG. 3 illustrates a cut away view of the drug delivery device 100 and needle assembly 101 of FIG. 2. The main body 102 of the drug delivery device houses a cartridge 114 of medicament to be delivered by the drug delivery device 100. The main body 102 also has a drive mechanism recess 116 for retaining the drive mechanism of the drug delivery device 100. The drive mechanism (not shown) may comprise a pre-stressed spring or may comprise a battery powered mechanism. The cartridge 114 comprises a plunger 118 configured to slide within the cartridge. When activated, the drive mechanism is configured to exert a force on the plunger 118 to cause it to advance within the cartridge 114. The cartridge 114 also comprises a septum 120 at its distal end. The plunger 118 and septum 120 seal the cartridge 114 until the septum 120 is pierced by the needle.

The needle assembly 101 further comprises a needle holder 122, a needle shield 124, and a sleeve 136. The proximal end of the sleeve 136 is secured to the distal end of the main body 102. The needle holder 122, needle shield 124, and remainder of the sleeve 136 are initially retained within the cap 104. The needle holder 122 supports a double ended needle 128 (which is an example of the needle 17 of FIGS. 1A and 1B).

Figure 4:
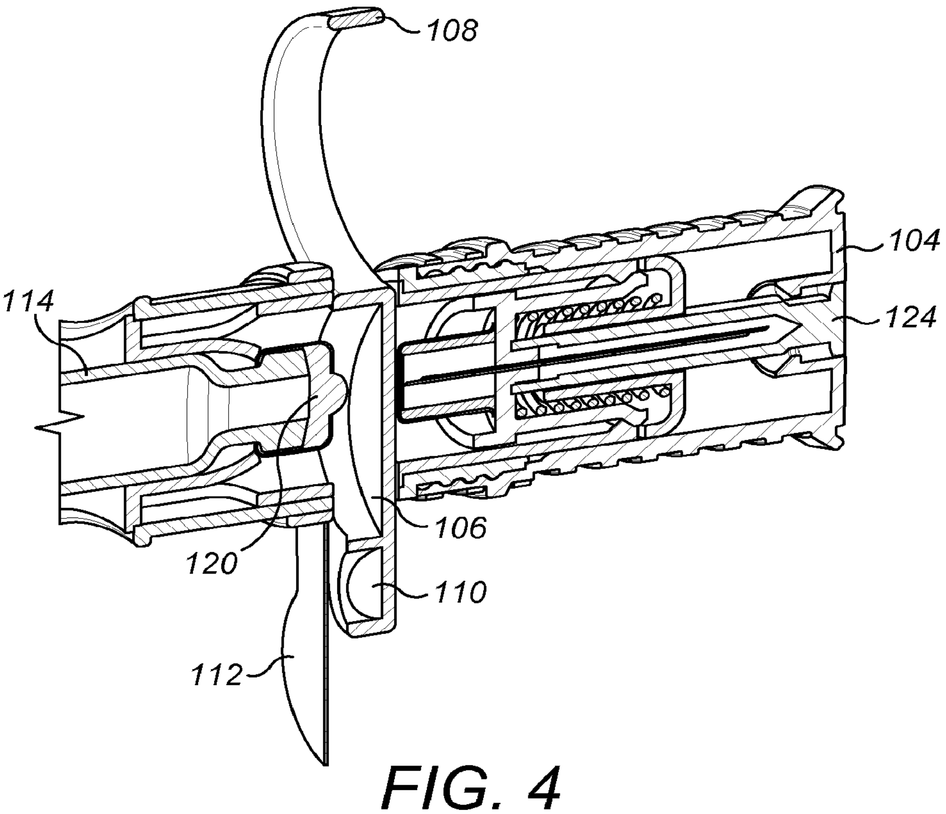
FIG. 4 is a cutaway view of a portion of the drug delivery device and a first embodiment of the needle assembly.
Figure 5:
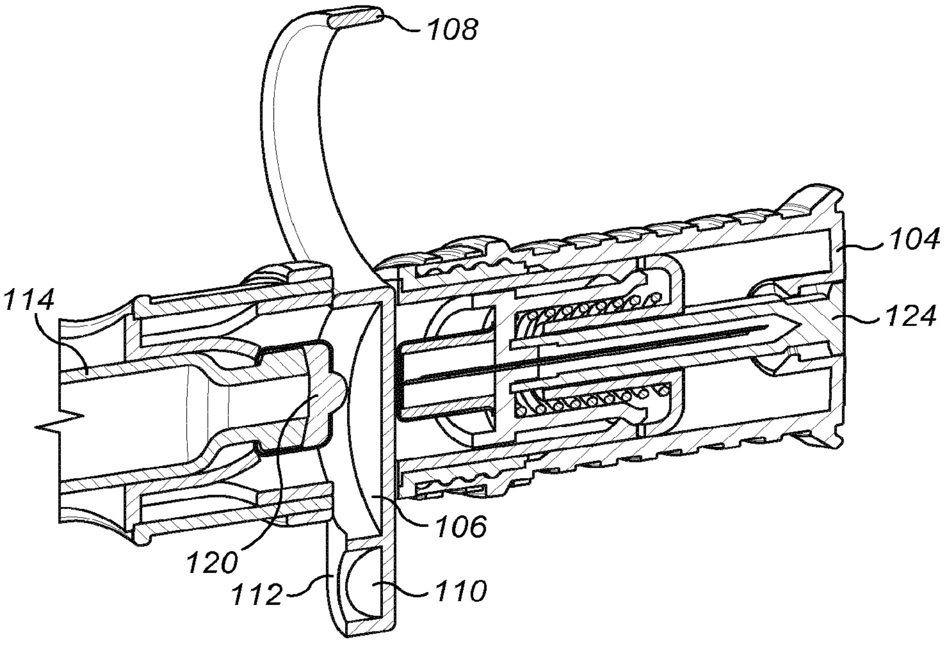
FIG. 5 is a cutaway view of a portion of the drug delivery device and a second embodiment of the needle assembly.

Referring now to FIGS. 4 and 5, cutaway views of a portion of the drug delivery device 100 are shown. FIG. 4 shows a first embodiment in which the sterile seal 112 has a user graspable protrusion, which is not secured to the removable member 106. Before removing the removable member 106, the user first physically removes the sterile seal 112 from the disinfectant swab 110. The user then engages the user graspable portion 108 and pulls the removable member 106 upwards. This movement causes the disinfectant swab 110 to slide past the septum 120 of the cartridge 114. The disinfectant swab 110 contacts the septum 120 and is dragged over it, causing the septum 120 to be sterilized. The presence of the removable member 106 in its initial position prevents the cap 104 from being removed from the needle assembly 101 and thus it is not possible to expose the needle 128 or perform an injection procedure without first sterilizing the septum 120 of the cartridge 114. This is advantageous as a user may otherwise forget to sterilize the equipment before performing an injection procedure. It will furthermore be clear to a user that they need to remove the removable member 106 before the cap 104 can be removed which gives a clear confirmation to the user that they have prepared the drug delivery device correctly.

Figure 6:
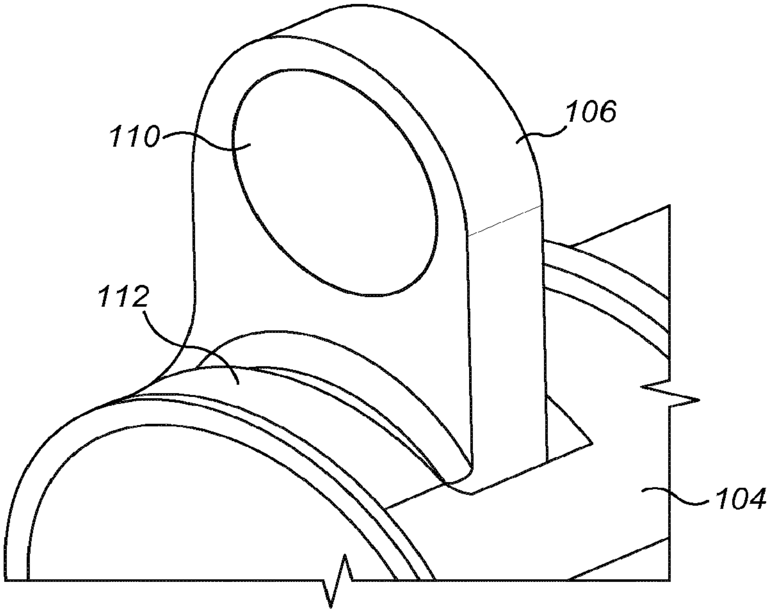
FIG. 6 is a close-up view of a removable member and disinfectant swab components of the needle assembly.

FIGS. 5 and 6 show a second embodiment in which the sterile seal 112 is permanently secured to the cap 104 of the needle assembly 101. In this embodiment, no user graspable protrusion is required. As with the embodiment of FIG. 4, the sterile seal 112 is releasable secured to the part of the removable member 106 retaining the disinfectant swab 110 such that the sterile seal 112 can be removed and the disinfectant swab 110 exposed. In the embodiment show in FIGS. 5 and 6, the sterile seal 112 is removed by action of the user removing the removable member 106. As the user pulls the removable member 106 upwards, the permanent attachment of the sterile seal 112 to the cap 104 of the needle assembly 101 causes the sterile seal 112 to be released from the disinfectant swab 110.

FIG. 6 is a close-up view of the removable member 106 and disinfectant swab 110 protruding from the lower aperture of the cap 104, before the removable member 106 has been removed. As can be seen, the sterile seal 112 completely covers the disinfectant swab 110 and has an extension, which is permanently secured to the cap 104. It will be appreciated that the sterile seal may equally be secured to the main housing 102 of the drug delivery device as well or in addition to being secure to the cap 104.

Figure 7:
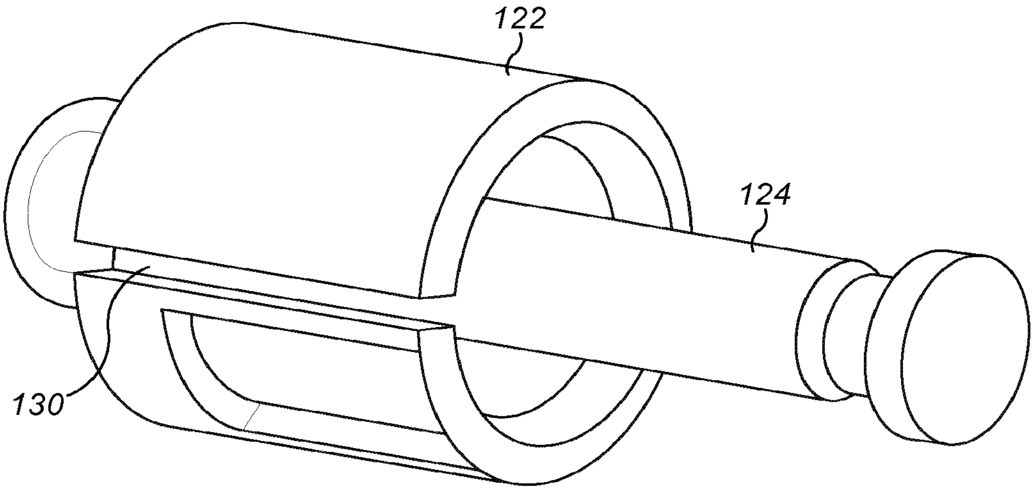
FIG. 7 shows some components of the needle assembly in greater detail.
Figure 8:
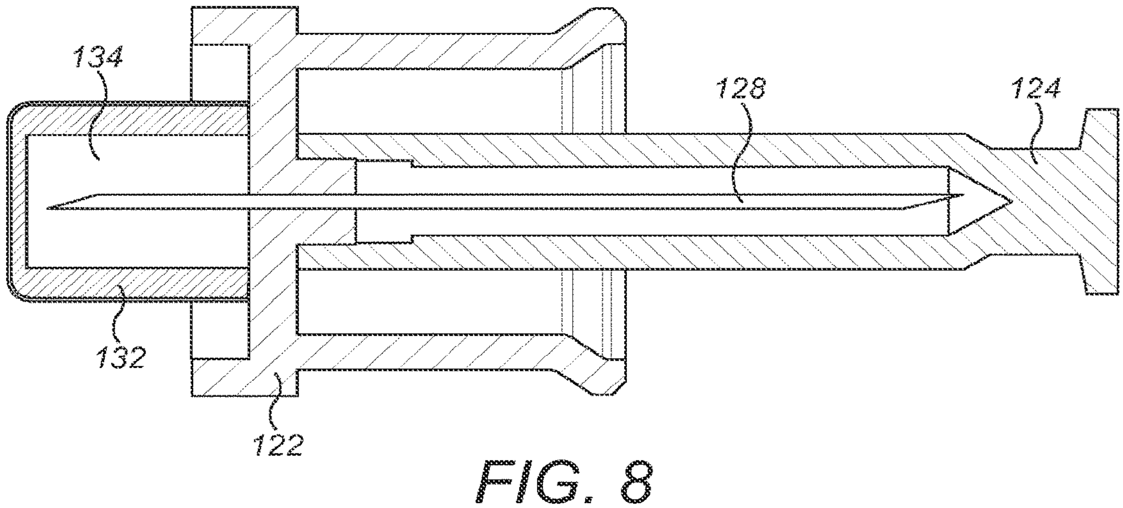
FIG. 8 is a cut-through view of the elements shown in FIG. 7.

FIGS. 7 and 8 illustrate some components of the needle assembly 101 in greater detail. The needle assembly 101 has a needle holder 122 having a generally hollow cylindrical shape and comprising one or more axially extending grooves 130 for guiding the needle holder 122 axially within the needle assembly 101. The needle 128 (not visible) is retained axially and centrally within the needle holder 122. The needle 128 is protected within the needle shield 124.

FIG. 8 is a cut-through view of the elements shown in FIG. 7, in which the double-ended needle 128 can be seen. The needle shield 124 has a friction connection to the needle holder 122 and can be physically removed by a user prior to activation of the drug delivery device 100. The proximal end of the double-ended needle 128 is protected by a solid foil 132 attached to the needle holder 122. The solid foil is in the form of a hollow cylinder with a solid end face. The space between the needle 128 and the solid foil 132 is filled with a compressible spacer material 134. The spacer material 134 protects the solid foil 132 from any damage by the needle 128 prior to activation of the drug delivery device 100.

Further components of the needle assembly 101 and exemplary operation of the needle assembly will now be described with reference to FIGS. 9 to 11.

Figure 9:
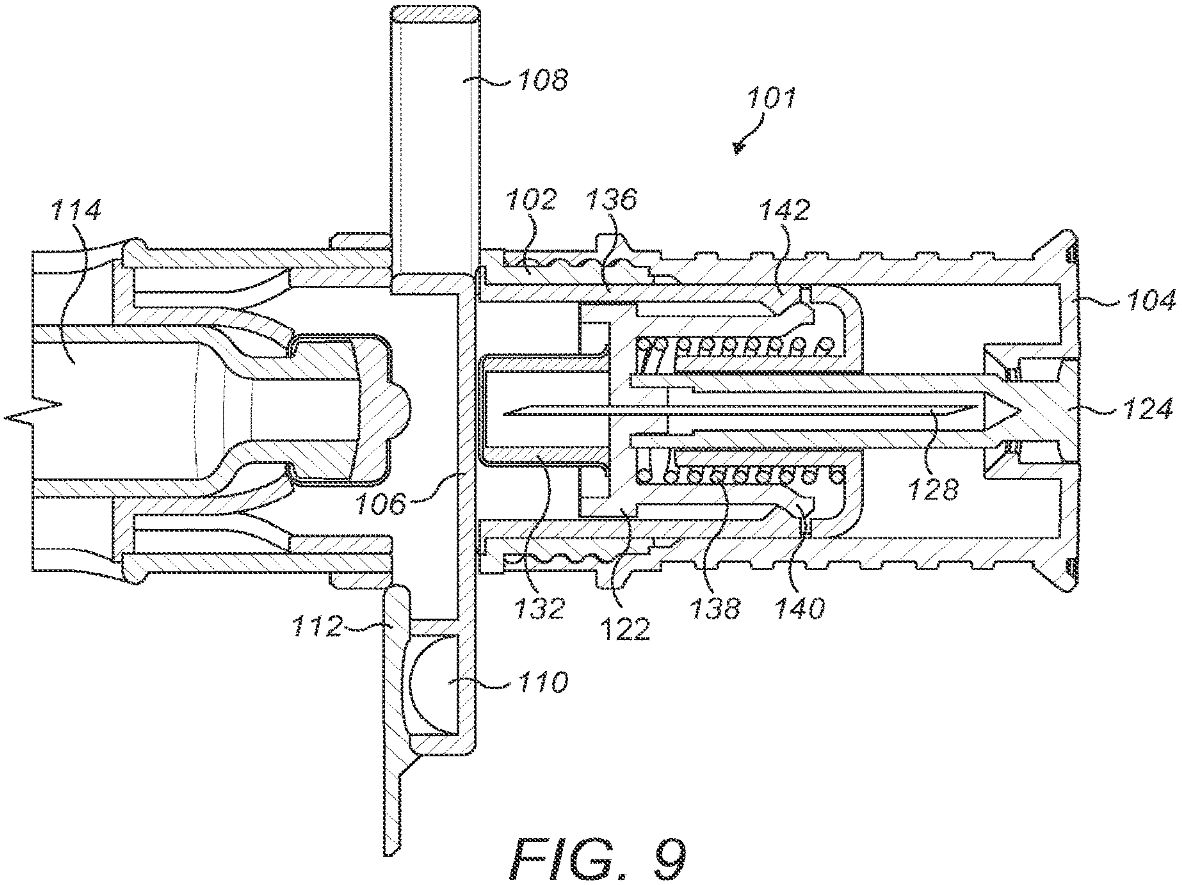
FIG. 9 shows the needle assembly in an initial state.

FIG. 9 shows the needle assembly 101 and cartridge 114 in an initial position. The needle assembly 101 comprises the removable member 106, cap 104, needle holder 122, needle shield 124, and sleeve 136 as previously described. The sleeve 136 is retained within and fixed to the main body 102 of the drug delivery device 100. The sleeve 136 is positioned within the cap 104 when the cap is attached. The needle holder 122 is retained within the sleeve 136 and is axially slidable relative thereto. The sleeve 136 may have one or more protrusions (not shown) which engage with the axial grooves 130 of the needle holder 122 in order to guide the needle holder to move axially within the sleeve 136. Alternatively, the needle holder 122 may comprise one or more protrusions and the sleeve 136 may comprise one or more corresponding grooves. A pre-stressed resilient element is provided between the sleeve 136 and the needle holder 122. The pre-stressed element may be a pre-compressed spring 138 as shown in FIGS. 9 to 11. The pre-compressed spring 138 biases the needle holder 122 proximally, away from the sleeve 136 and toward the main body 102 of the drug delivery device 100.

The needle holder 122 has one or more protrusions 140 at its distal end. The one or more protrusions 140 may take the form of a single annular flange. The sleeve 136 has one or more clips 142 at its distal end, which abut the one or more protrusions 140 of the needle holder 122. The clips 142 may take the form of inwardly protruding hooks. The clips 142 of the sleeve 136 may be resiliently deformable in a direction away from the centerline of the needle assembly 101. Alternatively or additionally, the entire distal end of the sleeve 136 may be deformable in direction away from the centerline of the needle assembly 101. The sleeve 136 is initially prevented from deforming by being surrounded by the cap 104. The needle holder 122 is prevented from moving relative to the sleeve 136 by the presence of the removable member 106 and the clips 142.

A user first removes the sterile seal 112 covering the disinfectant swab 110. The user then grasps user graspable portion 108 and slides the removable member 106 out of the needle assembly 101. During this action, the disinfectant swab 110 is pulled across the septum 120 of the cartridge 114, causing the septum 120 to be sterilized. Alternatively, the sterile seal 112 may be secured to the cap 104 or main body 102 such that it is removed as the removable member 106 is pulled from the needle assembly 101. Only after the removable member 106 is removed is the cap 104 free to rotate or move axially relative to the other components of the needle assembly 101.

Figure 10:
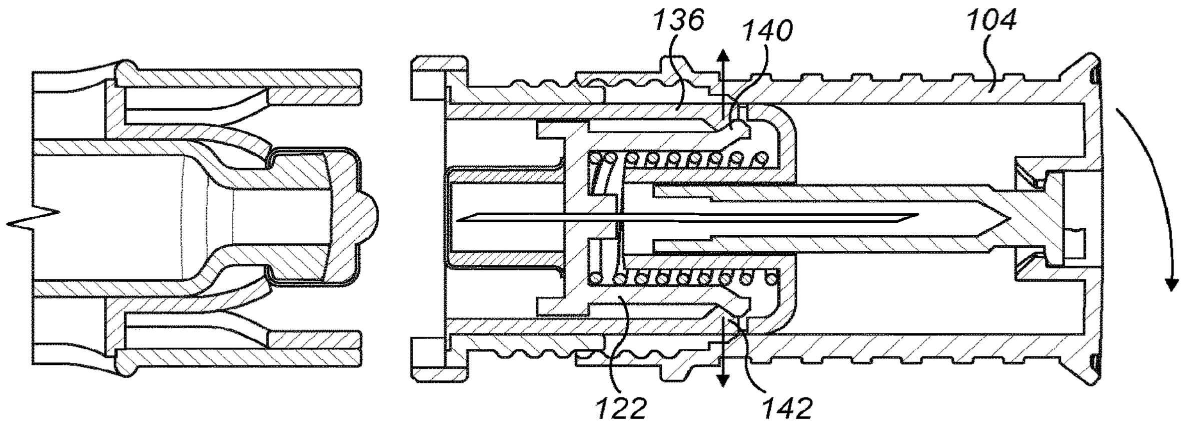
FIG. 10 shows the needle assembly in an intermediate state in which the removable member has been removed and the cap rotated.

Referring now to FIG. 10, after the removable member 106 has been removed the user rotates the cap 104. In some embodiments, the cap 104 is secured to the main body 102 by a threaded connection, such that as the user rotates the cap it moves distally relative to the main body 102 and remaining components of the needle assembly 101. Alternatively, the cap 104 is secured to the main body 102 by a bayonet connection, such that after the cap has been rotated by a predetermined amount, it is then free to move distally. In embodiments where the cap 104 is secured by a threaded connection, the thread may be several turns in length, for example at least three whole turns in length. This may ensure that it takes a user several seconds to move the cap from its initial position to the position shown in FIG. 10 (which may be referred to herein as an intermediate position). This may be done in order to allow sufficient time to ensure that the septum 120 of the cartridge 114 has been properly sterilized by action of the medicinal alcohol in the disinfectant swab 110 before the septum is pierced by the needle 128. A sufficient time may be, for example, at least 3 seconds.

The internal diameter of the cap 104 is larger at its proximal end than at its distal end. When the cap 104 reaches the axial position shown in FIG. 10, the internal surface of the cap 104 no longer contacts the sleeve 136. This allows the clips 142, or entire distal end of the sleeve 136, to deform outwards (as indicated by the arrows in FIG. 10), under the force provided by the pre-compressed spring 138. This allows the protrusions 140 to move distally past the clips 142 and the needle holder 122 slides axially within the sleeve 136. When the cap 104 reaches the intermediate position shown in FIG. 10, it may no longer be secured to the main body 102 of the drug delivery device 100 and may be removed. Alternatively further rotation of the cap 104 may be required before is it unsecured from the drug delivery device 100.

Figure 11:
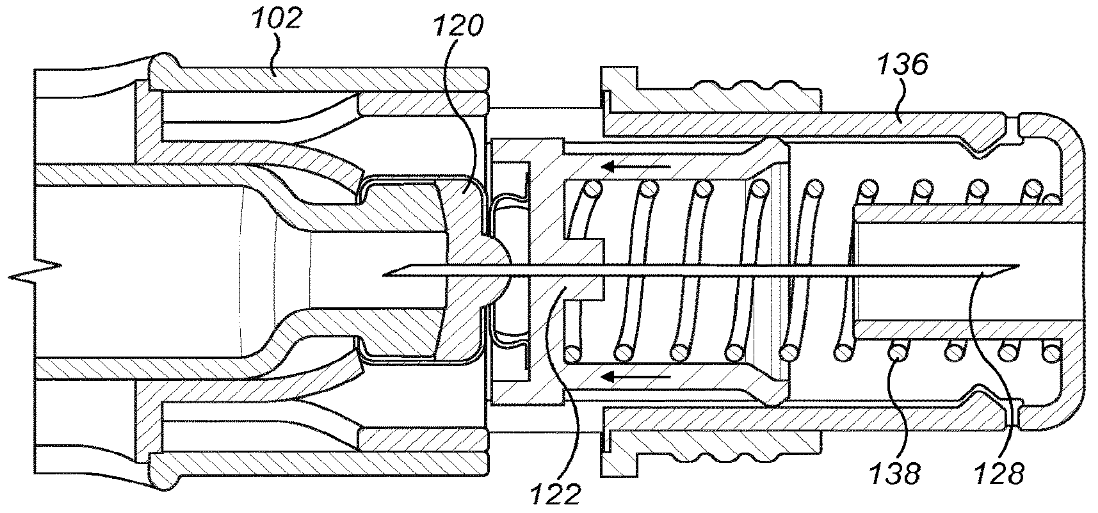
FIG. 11 shows the needle assembly in a final state in which the cap has been removed and the cartridge pierced by the needle.

As shown in FIG. 11, the needle holder 122 continues to move axially under force from the spring 138. The solid foil 132 contacts the septum 120 and the compressible spacer material 134 is compressed under force form the spring 138. The distal end of the double-ended needle 128 passes through the spacer material 134 and pierces the solid foil 132. The needle 128 then pierces the septum 120 and passes into the medicament chamber of the cartridge 114. The drug delivery device 100 is then ready for a medicament injection process to be formed.

The terms “drug” or “medicament” are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term “drug delivery device” shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or “drug container” adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis, and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term “derivative” refers to any substance, which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof

The invention claimed is:

1. A drug delivery device comprising:
a housing;
a medicament container disposed within the housing, the medicament container comprising a septum;
a movable member disposed within the housing, the movable member comprising a cleaning surface configured to contact the septum to at least partially clean or sterilize the septum; and
a needle configured to pierce the septum after the cleaning surface of the movable member contacts the septum to at least partially clean or sterilize the septum,
wherein the movable member is configured to move relative to the medicament container along a direction substantially perpendicular to a longitudinal axis of the medicament container to at least partially clean or sterilize the septum.

2. The drug delivery device of claim 1, wherein the cleaning surface comprises a disinfectant swab or sponge configured to contact the septum to at least partially clean or sterilize the septum.

3. The drug delivery device of claim 1, wherein the medicament container contains a medicament.

4. The drug delivery device of claim 3, wherein the drug delivery device is configured to expel the medicament through the needle after the needle pierces the septum and the needle is in fluid connection with the medicament of the medicament container.

5. A drug delivery device, comprising:
a housing;
a medicament container disposed within the housing, the medicament container comprising a septum;
a movable member disposed within the housing, the movable member comprising a cleaning surface configured to contact the septum to at least partially clean or sterilize the septum;
a needle configured to pierce the septum after the cleaning surface of the movable member contacts the septum to at least partially clean or sterilize the septum, and
a cap removably attached to a distal end of the housing, the drug delivery device configured to limit proximal movement of the needle relative to the housing while the cap is attached to the distal end of the drug delivery device.

6. The drug delivery device of claim 5, wherein the drug delivery device is configured to prevent removal of the cap from the distal end of the housing when the movable member is between the needle and the septum.

7. The drug delivery device of claim 6, wherein the drug delivery device is configured to allow removal of the cap from the distal end of the housing when the movable member is removed from the housing.

8. The drug delivery device of claim 5, wherein the movable member is configured to move through at least one opening of the cap to prevent the cap from being removed from the distal end of the housing when the movable member is positioned within the at least one opening of the cap.

9. The drug delivery device of claim 5, comprising a spring configured to bias the needle towards the septum such that removal of the cap from the distal end of the housing causes the needle to pierce the septum.

10. The drug delivery device of claim 5, wherein the medicament container contains a medicament.

11. The drug delivery device of claim 10, wherein the drug delivery device is configured to expel the medicament through the needle after the needle pierces the septum and the needle is in fluid connection with the medicament of the medicament container.

12. A method comprising:

moving a movable member of a drug delivery device relative to a medicament container of the drug delivery device to cause a cleaning surface of the movable member to contact a septum of the medicament container to at least partially clean or sterilize the septum; and after the cleaning surface contacts the septum, moving a needle relative to the septum to pierce the septum, wherein moving the movable member relative to the medicament container comprises moving the movable member along a direction substantially perpendicular to a longitudinal axis of the medicament container.

13. The method of claim 12, comprising deforming a material surrounding the needle when the material is compressed between the septum and a needle holder that supports the needle.

14. The method of claim 12, comprising expelling a medicament of the medicament container through the needle after the needle has pierced the septum.

15. The method of claim 12, comprising releasing an engagement between a needle holder supporting the needle and a sleeve to cause the needle to move relative to the septum to pierce the septum under a biasing force of a spring.

16. A method comprising:

moving a movable member of a drug delivery device relative to a medicament container of the drug delivery device to cause a cleaning surface of the movable member to contact a septum of the medicament container to at least partially clean or sterilize the septum;

after the cleaning surface contacts the septum, moving a needle relative to the septum to pierce the septum; and preventing a cap of the drug delivery device from being removed from a distal end of a housing of the drug delivery device by an engagement between the cap and the movable member.

17. The method of claim 16, comprising limiting a proximal movement of the needle relative to the septum while the cap is positioned on the distal end of the housing.

18. The method of claim 16, wherein moving the movable member relative to the medicament container from a first position in which the movable member is between the needle and the septum to a second position in which the movable member is removed from the housing causes a removal of the engagement between the cap and the movable member.

19. The method of claim 18, comprising removing the cap from the distal end of the drug delivery device after the engagement between the cap and the movable member has been removed.

20. The method of claim 16, comprising expelling a medicament of the medicament container through the needle after the needle has pierced the septum.

21. The method of claim 16, comprising releasing an engagement between a needle holder supporting the needle and a sleeve to cause the needle to move relative to the septum to pierce the septum under a biasing force of a spring.

22. A method comprising:

moving a movable member of a drug delivery device relative to a cap of the drug delivery device to release an engagement between the movable member and the cap, the engagement preventing the cap from being removed from the drug delivery device;

at least partially cleaning or sanitizing a septum of a medicament container of the drug delivery device with a cleaning surface of the movable member as the movable member moves relative to the cap; and after at least partially cleaning or sanitizing the septum, removing the cap to cause a needle to move relative to the septum and pierce the septum under a biasing force of a spring.

* * * * *